(12) United States Patent
Castel

(10) Patent No.: US 9,931,499 B2
(45) Date of Patent: Apr. 3, 2018

(54) METHOD AND APPARATUS FOR PROVIDING TOPICAL ANESTHESIA PRIOR TO AND DURING A COSMETIC PROCEDURE

(71) Applicant: J. Chris Castel, Reno, NV (US)

(72) Inventor: J. Chris Castel, Reno, NV (US)

(73) Assignee: CAREWEAR CORP., RENO, NV (US)

( * ) Notice: Subject to any disclaimer, the term of this patent is extended or adjusted under 35 U.S.C. 154(b) by 946 days.

(21) Appl. No.: 13/897,762

(22) Filed: May 20, 2013

(65) Prior Publication Data

US 2013/0253414 A1 Sep. 26, 2013

Related U.S. Application Data

(62) Division of application No. 12/792,000, filed on Jun. 2, 2010, now Pat. No. 8,449,522.

(Continued)

(51) Int. Cl.
*A61N 1/04* (2006.01)
*A61K 8/02* (2006.01)
(Continued)

(52) U.S. Cl.
CPC .............. *A61N 1/0456* (2013.01); *A61K 8/02* (2013.01); *A61M 19/00* (2013.01);
(Continued)

(58) Field of Classification Search
CPC .... A61N 1/0456; A61N 1/0472; A61N 1/325; A61N 1/36021; A61N 1/0428; A61K 8/02; A61M 19/00
See application file for complete search history.

(56) References Cited

U.S. PATENT DOCUMENTS

| 4,141,359 | A | * | 2/1979 | Jacobsen | ............... A61N 1/325 604/20 |
| 4,406,658 | A | * | 9/1983 | Lattin | .................... A61N 1/044 604/20 |

(Continued)

OTHER PUBLICATIONS

International Search Report/Written Opinion dated Jul. 30, 2010 for PCT Application No. PCT/US2010/037020.

*Primary Examiner* — Theodore Stigell
(74) *Attorney, Agent, or Firm* — Stinson Leonard Street LLP

(57) ABSTRACT

A method and apparatus for iontophoretically administering an anesthetic medicament and simultaneously providing electroanesthesia to a patient is provided. The apparatus comprises a generator operable to produce an electrical current comprised of a direct current superimposed with either an alternating current or a pulsed direct current. A conductive mask is configured to cover the anesthetic medicament applied to a treatment area on the skin of the patient, wherein the conductive mask includes an electrical contact connectable to the generator for receiving the electrical current such that the conductive mask functions as an electrode. One or more additional electrodes are applied to the skin of the patient, wherein each of the additional electrodes is connectable to the generator for receiving the electrical current. At least one of the additional electrodes may comprise a conductive applicator for a cosmetic treatment device.

28 Claims, 7 Drawing Sheets

Related U.S. Application Data

(60) Provisional application No. 61/183,684, filed on Jun. 3, 2009.

(51) Int. Cl.
*A61M 19/00* (2006.01)
*A61N 1/32* (2006.01)
*A61N 1/36* (2006.01)
*A61Q 19/00* (2006.01)

(52) U.S. Cl.
CPC ......... *A61N 1/0428* (2013.01); *A61N 1/0472* (2013.01); *A61N 1/325* (2013.01); *A61N 1/36021* (2013.01); *A61Q 19/00* (2013.01); *A61K 2800/83* (2013.01); *A61K 2800/884* (2013.01)

(56) References Cited

U.S. PATENT DOCUMENTS

| | | |
|---|---|---|
| 5,169,384 A | 12/1992 | Bosniak et al. |
| 2001/0007949 A1* | 7/2001 | Silverstone ........ A61N 1/36021 607/45 |
| 2002/0173743 A1* | 11/2002 | Tapper ................... A61N 1/044 604/20 |
| 2003/0028124 A1 | 2/2003 | Tapper |
| 2005/0234516 A1* | 10/2005 | Gueret ................... A61N 1/328 607/3 |
| 2005/0286966 A1* | 12/2005 | Gueret ................... A45D 34/04 401/130 |
| 2006/0149337 A1* | 7/2006 | John ................. A61N 1/36082 607/45 |
| 2007/0260169 A1 | 11/2007 | Hause |
| 2008/0199830 A1* | 8/2008 | Fontenot ............. A46B 5/0012 433/215 |

\* cited by examiner

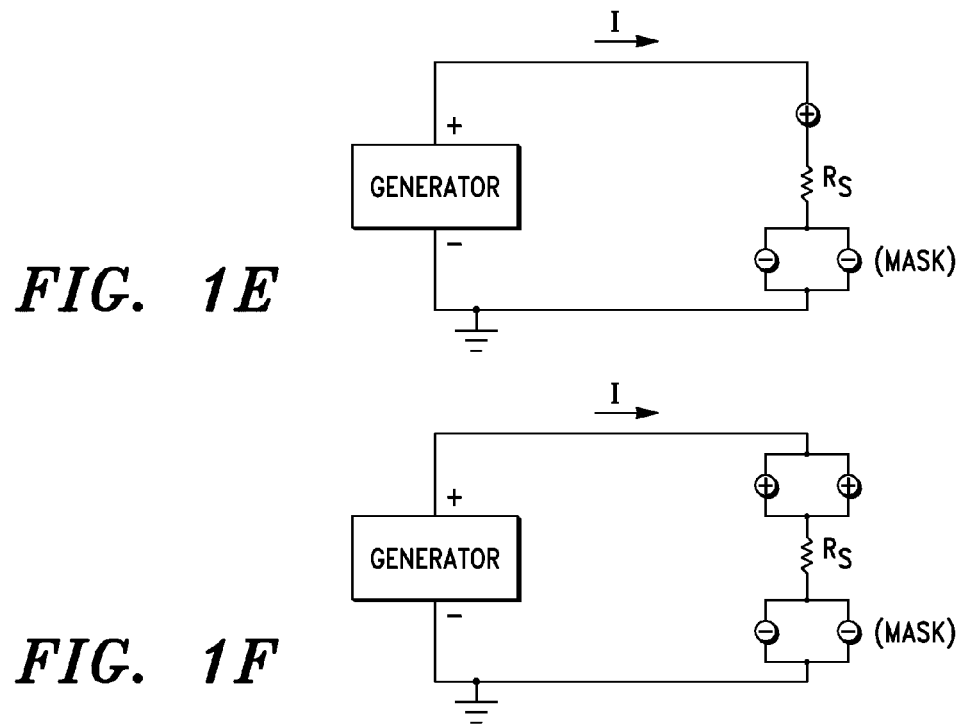
*FIG. 1E*
*FIG. 1F*
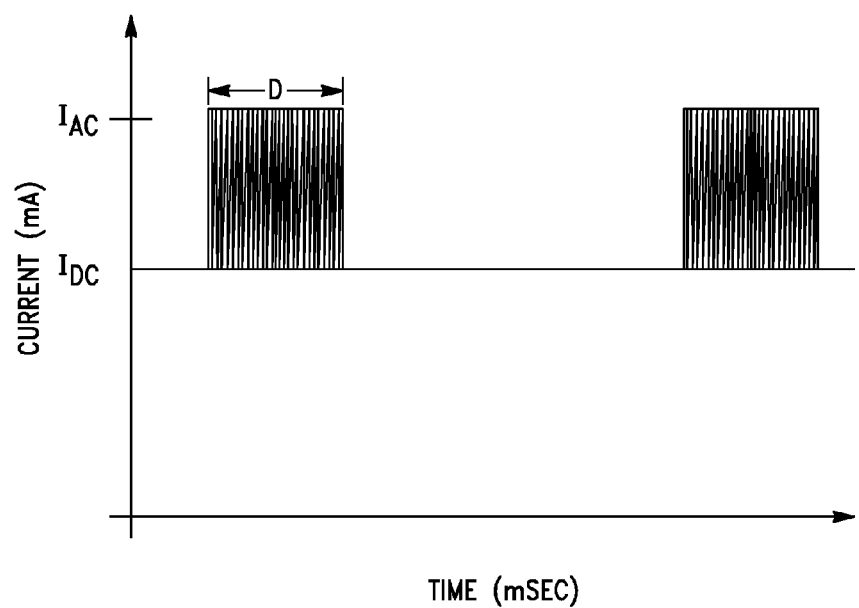
*FIG. 2*

METHOD AND APPARATUS FOR PROVIDING TOPICAL ANESTHESIA PRIOR TO AND DURING A COSMETIC PROCEDURE

CROSS-REFERENCE TO RELATED APPLICATIONS

This application is a divisional of U.S. application Ser. No. 12/792,000 filed on Jun. 2, 2010, now U.S. Pat. No. 8,449,522, which is based on and claims priority to U.S. Provisional Patent Application Ser. No. 61/183,684 filed on Jun. 3, 2009, which are both incorporated herein by reference.

STATEMENT REGARDING FEDERALLY SPONSORED RESEARCH OR DEVELOPMENT

Not applicable.

FIELD OF THE INVENTION

The present invention relates generally to the provision of anesthetic effects in patients and, more particularly, to a system and method for providing topical anesthesia to a patient prior to and during a cosmetic procedure.

SUMMARY OF THE INVENTION

The present invention is directed to a method and apparatus for iontophoretically administering an anesthetic medicament and providing electroanesthesia to a patient prior to and during a cosmetic procedure. Prior to the cosmetic procedure, an anesthetic medicament is applied to the surface of the patient's skin where the anesthetic effect is desired (e.g., the area to be treated during the cosmetic procedure). Next, a conductive mask (which functions as an electrode) and one or more associated electrodes are applied to the surface of the skin. In general, the conductive mask should be shaped to cover the areas to be treated during the cosmetic procedure (e.g., the entire face, the forehead area, the lip area, etc.). The associated electrodes may be incorporated into one or more separable portions of the conductive mask, may be applied to the patient separately from the conductive mask, or any combination thereof. An electrical current is then applied to the conductive mask and associated electrodes. The electrical current preferably comprises a DC current superimposed with either an AC current or a pulsed DC current, which is used to iontophoretically administer the anesthetic medicament and simultaneously provide electroanesthesia to the patient.

Following the iontophoretic administration of the anesthetic medicament, all or a portion of the conductive mask is removed (depending on the configuration of the conductive mask) so as to expose the treatment area for the cosmetic procedure. During the cosmetic procedure, electrical stimulation to the selective superficial nerves is maintained so as to provide electroanesthesia to the patient. This electrical stimulation may be applied via the associated electrodes discussed above (i.e., electrodes incorporated into the separable portion(s) of the conductive mask and/or electrodes separately positioned on the skin of the patient). In addition, one of the electrodes may comprise a conductive applicator coupled to the end or tip of the cosmetic treatment device, which is in contact with the skin during the cosmetic procedure.

BRIEF DESCRIPTION OF THE DRAWINGS

FIGS. 1A-1F are diagrams of various electrode configurations that may be used to iontophoretically administer an anesthetic medicament and simultaneously provide electroanesthesia to a patient in accordance with the present invention.

FIG. 2 is a diagram of an exemplary waveform generated by the generator shown in FIGS. 1A-1F.

DETAILED DESCRIPTION OF EXEMPLARY EMBODIMENTS

Figure 1A:
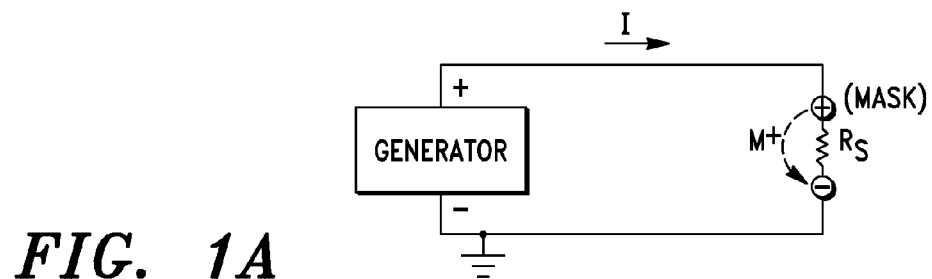

The present invention is directed to a method and apparatus for providing topical anesthesia to a patient during a cosmetic procedure. Examples of cosmetic procedures that would benefit from the provision of such topical anesthesia include LASER resurfacing, Fractal LASER applications, Plash Phototherapy, RF, ultrasound, and surgeries using scalpels or other cutting or remodeling devices. Of course, other types of cosmetic procedures are also within the scope of the invention. While the invention is particularly well-suited for facial cosmetic procedures, it should be understood that the topical anesthesia may also be provided to other body areas of a patient.

While the present invention will be described in detail below with reference to various exemplary embodiments, it should be understood that the invention is not limited to the specific configuration or methodology of these embodiments. In addition, although the exemplary embodiments are described as embodying several different inventive features, one skilled in the art will appreciate that any one of these features could be implemented without the others in accordance with the invention.

Exemplary Method

In general terms, the method of the present invention involves several steps that are performed prior to and during a cosmetic procedure. First, prior to the cosmetic procedure, an anesthetic medicament is applied to the surface of the skin where the anesthetic effect is desired (e.g., the area to be treated during the cosmetic procedure). The anesthetic medicament may comprise any conductive ionic molecule or compound that can be transdermally administered to a patient with an iontophoretic delivery system. Specific examples of anesthetic medicaments are provided below.

Next, a conductive mask (which functions as an electrode) and one or more associated electrodes are applied to the surface of the skin. The conductive mask includes a conductive element and is preferably coated with a hydrogel or other conductive gel to conform the mask to the skin surface and conduct current from the conductive element to the underlying tissue. The conductive gel may include, for example, a metal such as aluminum, carbon film or carbon film coated with a conductor such as silver, or silver chloride to reduce the potential for burns of the superficial tissue of the skin from the application of DC current. The configuration of the conductive mask and associated electrodes will vary, both in the shape of the conductive mask and the positioning of the electrodes. In general, the conductive mask should be shaped to cover the areas to be treated during the cosmetic procedure (e.g., the entire face, the forehead area, the lip area, etc.). The various electrodes may be incorporated into one or more separable portions of the conductive mask, may be applied to the patient separately from the conductive mask, may be a conductive applicator coupled to the end or tip of the cosmetic treatment device used to perform the cosmetic procedure (which is in contact with the skin during the cosmetic procedure), or any combination thereof. Various exemplary embodiments of the conductive mask and associated electrodes will be described below with reference to FIGS. 3-7.

Next, an electrical current is applied to the conductive mask and associated electrodes. The electrical current preferably comprises a DC current superimposed with either an AC current or a pulsed DC current, which is used to iontophoretically administer the anesthetic medicament and simultaneously provide electroanesthesia to the patient. The anesthetic medicament is iontophoretically administered via the application of the DC current, which causes delivery of the anesthetic medicament through the surface of the patient's skin into underlying tissues. Of course, it should be understood that the anesthetic medicament is transdermally delivered in the areas of the patient's skin that are covered by the conductive mask (i.e., the areas to be treated during the cosmetic procedure). In order to provide additional electroanesthesia, the combination DC current/AC current or DC current/pulsed DC current is used to provide electrical stimulation so as to stimulate or block selective superficial nerves of the patient. The DC current may also be used to optimize the fluid and pH balance under the treatment area for optimal coupling of the LASER or RF field used in the cosmetic procedure.

Finally, following the iontophoretic administration of the anesthetic medicament, all or a portion of the conductive mask is removed (depending on the configuration of the conductive mask) so as to expose the treatment area for the cosmetic procedure. During the cosmetic procedure, electrical stimulation to the selective superficial nerves is maintained so as to provide electroanesthesia to the patient. It will be seen that this electrical stimulation may be applied via electrodes that are incorporated into portion(s) of the conductive mask that are not removed prior to the cosmetic procedure, electrodes that are separately positioned on the skin of the patient, an electrode comprising a conductive applicator coupled to the end or tip of the cosmetic treatment device (which is in contact with the skin during the cosmetic procedure), or any combination thereof.

Exemplary Apparatus

Various electrode configurations for the apparatus of the present invention are shown diagrammatically in FIGS. 1A-1F. In each case, the apparatus includes a controllable waveform generator that is capable of producing a direct current superimposed with either an AC current or a pulsed DC current. The apparatus also includes a plurality of electrodes that may be applied to the skin of a patient, wherein the conductive mask itself functions as one of those electrodes. It should be noted that the position of such electrodes on the patient will be described below in connection with the exemplary embodiments of FIGS. 3-7.

FIG. 2 is a diagram of an exemplary waveform that may be produced by the controllable waveform generator shown in FIGS. 1A-1F, wherein the waveform is shown as a plot of time versus current. In this example, it can be seen that the waveform is a combination of DC current and AC current provided in rectangular pulses. The DC current is preferably applied using a constant voltage-constant current method during treatment. To do so, the controllable waveform generator preferably includes a voltage controller that allows the patient or clinician to pre-set a maximum voltage level upon receipt of the appropriate sensation or current dose. If the impedance of the circuit increases, the voltage remains constant at its pre-set limit. However, if the impedance decreases, the voltage will decrease proportionally to maintain a constant current to the underlying tissue. As such, the patient does not feel discomfort if an electrode or probe is removed from contact or recontacted with the surface of the patient's skin.

The current level of the DC current is shown as $I_{DC}$ in FIG. 2, which is preferably in the range of 0-10 mA. To prevent the occurrence of skin burns, the polarity of the DC current is preferably reversed at regular intervals, for example, every 1-5 minutes, using a ramp function to avoid startling the patient on the polarity change. In other words, the DC current is ramped down prior to a polarity change and ramped up following the polarity change. The current level of the AC current ranges from $I_{DC}$ to a peak current level shown as $I_{AC}$ in FIG. 2, which is preferably in the range of 0-100 mA. The carrier frequency of the AC current ranges from 5-200 kHz, as shown in FIG. 2. The carrier frequency may be operated continuously or burst modulated at duty factors ranging from 1-99%, preferably in the range of 10-50%, in the range of 0.5-1000 Hz burst rate, with frequencies between 1-15 Hz, 30-60 Hz, 40-70 Hz, 70-120 Hz and 750-1000 Hz being preferred. Each burst has a pulse duration D, as shown in FIG. 2. Preferably, D is in the range of 1-10 milliseconds and, most preferably, in the range of 1-5 milliseconds.

It should be understood that the controllable waveform generator is preferably capable of independently controlling many of the parameters characterizing the waveform shown in FIG. 2. It should also be understood that the waveform shown in FIG. 2 is merely an example of a waveform that may be produced by the generator, and other waveforms are within the scope of the present invention. For example, the AC current in FIG. 2 could be replaced with a pulsed DC current having the same parameters as those of the AC current described above. Of course, the hardware and firmware design of the generator will be apparent to one of ordinary skill in the art.

As discussed above, the method of the present invention allows for the provision of topical anesthesia to a patient via two different anesthetic mechanisms: (1) iontophoretic administration of anesthetic medicament prior to the cosmetic procedure (using DC current); and (2) electroanesthesia prior to and during the cosmetic procedure (using DC current superimposed with either AC current or pulsed DC current). Each of these anesthetic mechanisms will now be described in greater detail with reference to the diagrams shown in FIGS. 1A-1F.

Iontophoretic Administration of Anesthetic Medicament

Figure 1B:
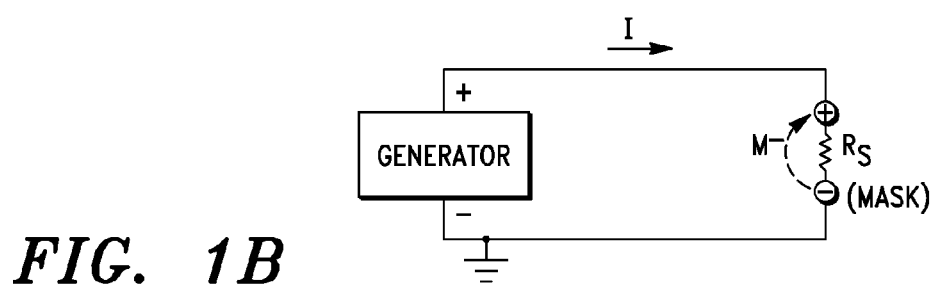

During iontophoresis, DC current is used to cause anesthetic medicament ions to move across the surface of the skin and diffuse into underlying tissue. To create an iontophoretic circuit, the positive and negative poles of the controllable waveform generator are electrically connected to positive and negative electrodes, respectively, applied to the skin of the patient. A positively charged medicament must be coupled to a conductive mask functioning as a positive electrode (as shown in FIGS. 1A, C and D). On the other hand, a negatively charged medicament must be coupled to a conductive mask functioning as a negative electrode (as shown in FIGS. 1B, E and F). Examples of common positive polarity medicaments include bupivacaine hydrochloride, calcium chloride, lidocaine hydrochloride, zinc chloride, and lidocaine. Examples of common negative polarity medicaments include acetic acid, betamethasone sodium phosphate, copper sulfate, dexamethasone sodium phosphate, fentinol, magnesium sulfate, naproxen sodium, sodium chloride, and sodium salicylate. Of course, other anesthetic medicaments are also within the scope of the present invention.

The simplified diagrams shown in FIGS. 1A and 1B are provided to compare the movement of anesthetic medicaments of positive and negative polarities, respectively, through the skin of a patient. In FIG. 1A, the conductive mask (which functions as a positive electrode) and a negative electrode are applied to the surface of the skin at separate locations. Aside from the conductivity of the patient's skin (which is made up primarily of fluids), these locations are electrically isolated from each other. The positive pole of the generator is coupled to the conductive mask/positive electrode, and the negative pole of the generator is coupled to the negative electrode. As such, electrical current (I) flows from the generator to the conductive mask/positive electrode and through the patient's skin to the negative electrode. The electromotive differential between the conductive mask/positive electrode and the negative electrode induces the positive polarity medicament to move as positive ions through the surface of the patient's skin in the direction of the negative electrode (as indicated by the dashed arrow labeled M$^+$). Of course, this electromotive differential must be sufficient to overcome the electrical resistance ($R_S$) of the patient's skin.

In FIG. 1B, the conductive mask (which functions as a negative electrode) and a positive electrode are applied to the surface of the skin at separate locations. Again, aside from the conductivity of the patient's skin, these locations are electrically isolated from each other. The positive pole of the generator is coupled to the positive electrode, and the negative pole of the generator is coupled to the conductive mask/negative electrode. As such, electrical current (I) flows from the generator to the positive electrode and through the patient's skin to the conductive mask/negative electrode. The electromotive differential between the positive electrode and the conductive mask/negative electrode induces the negative polarity medicament to move as negative ions through the surface of the patient's skin in the direction of the positive electrode (as indicated by the dashed arrow labeled M$^-$). Of course, this electromotive differential must be sufficient to overcome the electrical resistance ($R_S$) of the patient's skin.

Figure 1C:
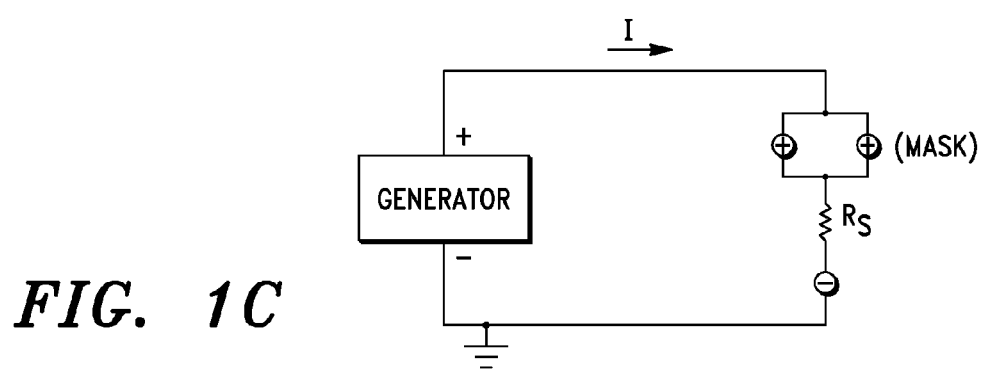
Figure 1D:
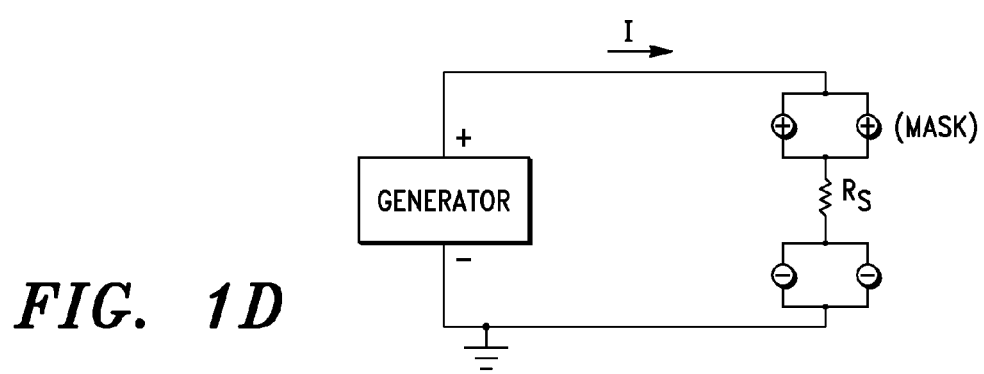

One skilled in the art will appreciate that a number of electrodes may be applied to the skin of the patient in accordance with the present invention. For example, the diagrams shown in FIGS. 1C and 1D are variations on the diagram shown in FIG. 1A (which is used for the application of a positive polarity medicament). FIG. 1C shows a pair of positive electrodes (in parallel) and a single negative electrode, while FIG. 1D shows a pair of positive electrodes (in parallel) and a pair of negative electrodes (in parallel). In either case, the mask (which functions as one of the positive electrodes) may be removed after administration of the anesthetic medicament and the remaining positive electrode may be used to provide electroanesthesia during the cosmetic procedure.

Similarly, the diagrams shown in FIGS. 1E and 1F are variations on the diagram shown in FIG. 1B (which is used for the application of a negative polarity medicament). FIG. 1E shows a single positive electrode and a pair of negative electrodes (in parallel), while FIG. 1F shows a pair of positive electrodes (in parallel) and a pair of negative electrodes (in parallel). In either case, the mask (which functions as one of the negative electrodes) may be removed after administration of the anesthetic medicament and the remaining negative electrode may be used to provide electroanesthesia during the cosmetic procedure.

Electroanesthesia

In order to provide electroanesthesia, the generator shown in FIGS. 1A-1F may be used to produce a DC current superimposed with either an AC current or a pulsed DC current (such as the exemplary waveform shown in FIG. 2) that is applied to electrodes positioned on the patient's skin over selective superficial nerves. This electrical current stimulates the superficial nerves so as to elicit analgesia by stimulating the peripheral and central release of substances such as endorphins, enkephalins, dynorphins, and serotonin when the correct spectrum of the modulated signal is provided. The signal is optimized when a negative DC current is superimposed with the pulsed DC or AC signal as it lowers the peripheral nerve firing threshold making it easier for the current to activate peripheral nerves such as A delta and C fibers. As discussed above, the DC current may also be used for its iontophoretic effects to push through an anesthetic medicament and may also be used to optimize the fluid and pH balance under the treatment area for optimal coupling of the LASER or RF field used in the cosmetic procedure. The frequencies in the range of 30-65 Hz are particularly important as they represent the firing rates of A delta fibers responsible for acute pain phasic response from initial surgical or procedural insult. When activated, these fibers provide a descending inhibitory signal that blocks pain segmentally. This is often referred to as DNIC, or diffuse noxious inhibitory control, and is a well-established mechanism of pain relief. When the DC current is superimposed the threshold of these fibers can be dropped so as to allow them to be activated at lower current densities, providing a more comfortable activation of DNIC. The currents can also be provided through the LASER or treatment handpiece directly to the target tissue to provide an additional level of pain control (anesthetic effect). When used in conjunction with pre-treatment iontophoresis to push an appropriate anesthetic medicament through the target tissue, profound anesthetic effect occurs in the superficial tissues.

In an alternative approach, the current can be used to block the nerves. If the AC or pulsed DC current is run continuously without modulation at carrier frequencies typically above 1000 Hz but more optimally above 10,000 Hz, and positive current is applied over the nerves to be anesthetized, the following effects will take place: (1) the nerve firing threshold will be raised by the positive DC current; and (2) the AC or pulsed DC current will cause a local nerve block known as wedenski inhibition (reactive depolarization) as the nerves are not able to repolarize at these high frequencies of stimulation, thus losing their ability to conduct pain. The currents can also be provided through the LASER or treatment handpiece directly to the target tissue to provide an additional level of pain control (anesthetic effect). When used in conjunction with pre-treatment iontophoresis to push an appropriate anesthetic medicament through the target tissue, profound anesthetic effect occurs in the superficial tissues.

Referring to the diagrams shown in FIGS. 1A-1F, it can be seen that various electrode configurations may be used to provide electroanesthesia in accordance with the present invention. Any of these electrode configurations are suitable for providing electroanesthesia prior to the cosmetic procedure (i.e., simultaneously with the iontophoretic administration of the anesthetic medicament). However, as discussed below, the electrode configurations shown in FIGS. 1C-1F are preferred in that they also allow the provision of electroanesthesia during the cosmetic procedure after the conductive mask has been removed.

The electrode configurations shown in FIGS. 1A and 1B include a single positive electrode and a single negative electrode. One of these electrodes comprises the conductive mask that is used to iontophoretically administer the anesthetic medicament (i.e., the positive electrode in FIG. 1A and the negative electrode in FIG. 1B). The other electrode (i.e., the negative electrode in FIG. 1A and the positive electrode in FIG. 1B) may be positioned in various locations on the skin of the patient, such as over the masseter or posterior sub-occipital areas. Of course, other locations are also within the scope of the present invention. While this electrode configuration may be used to provide electroanesthesia prior to the cosmetic procedure, it would not be suitable for providing electroanesthesia during the cosmetic procedure after the conductive mask has been removed.

The electrode configurations shown in FIGS. 1C and 1E are the same as those in FIGS. 1A and 1B, with the exception that they include an additional electrode having the same polarity as the conductive mask (i.e., an additional positive electrode in FIG. 1C and an additional negative electrode in FIG. 1E). This additional electrode may be used to provide electroanesthesia during the cosmetic procedure after the conductive mask has been removed. This additional electrode may be positioned in various locations on the skin of the patient, such as on the lower forehead area of the patient (centered above the eyes). Alternatively, this additional electrode may comprise a conductive applicator that is coupled to the end or tip of the cosmetic treatment device, which is in contact with the skin during the cosmetic procedure. Of course, other locations are also within the scope of the present invention.

The electrode configurations shown in FIGS. 1D and 1F are the same as those in FIGS. 1C and 1E, with the exception that they include an additional electrode having the opposite polarity as the conductive mask (i.e., an additional negative electrode in FIG. 1D and an additional positive electrode in FIG. 1F). This additional electrode may be used to provide bilateral placement of the electrodes over the masseter or posterior sub-occipital areas, or any other location within the scope of the present invention. The bilateral electrode placement provides a bilateral effect to the anesthesia as current flows over nerves enervating both sides of the face. Many of these nerves overlap each other and, thus, the bilateral return electrodes provide a more profound, less spotty anesthetic effect.

Various exemplary embodiments of the present invention will now be described with reference to FIGS. 3-7.

First Exemplary Embodiment

Figure 3:
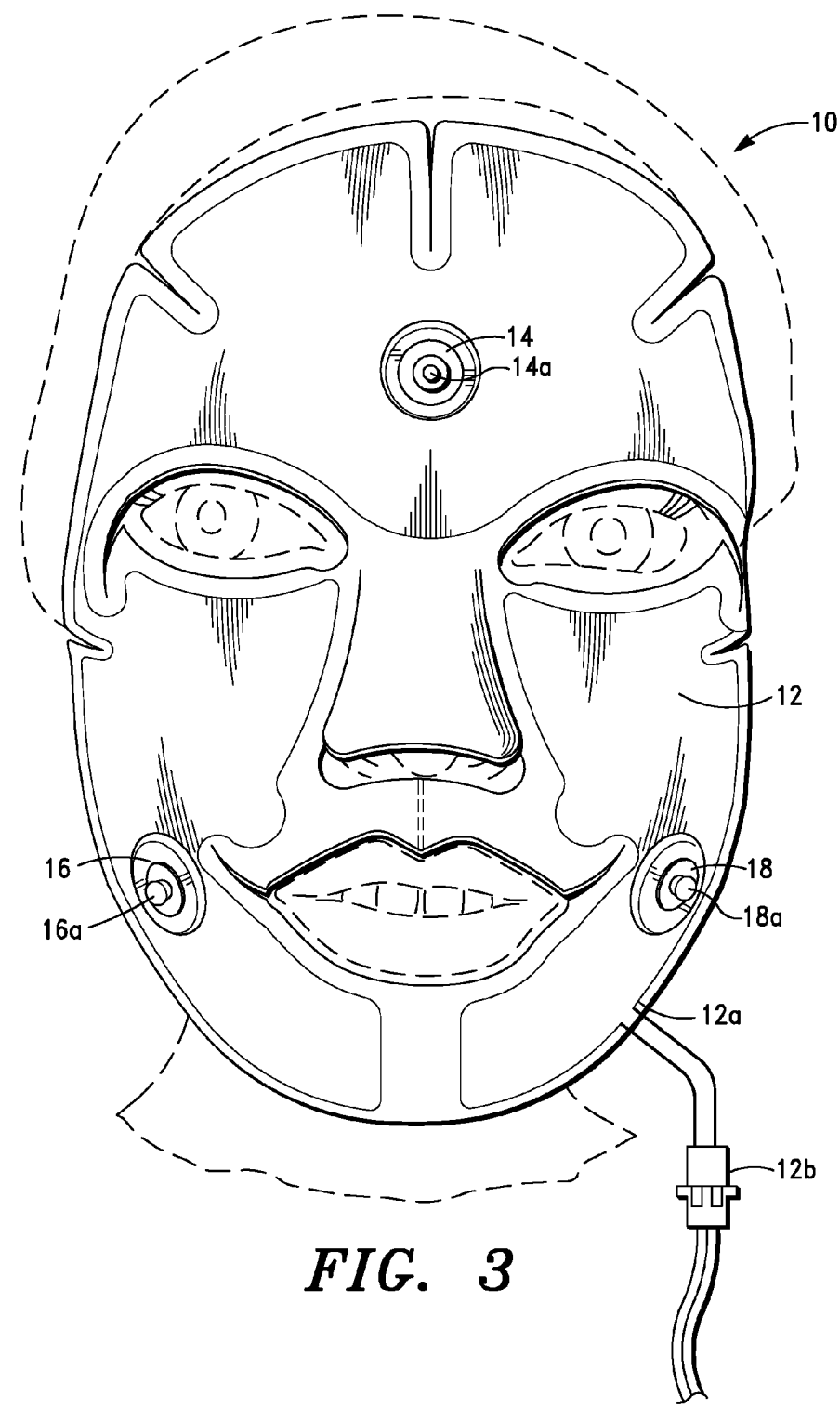
FIG. 3 is a drawing of a conductive mask in accordance with a first exemplary embodiment of the present invention, wherein the conductive mask includes a main mask portion applied to substantially the entire face of a patient (which functions as an electrode), a mask portion positioned on the lower forehead of the patient (which functions as an electrode), and two mask portions positioned bilaterally on the masseter areas of the patient (each of which functions as an electrode).

Referring to FIG. 3, a conductive mask and associated electrodes in accordance with a first exemplary embodiment of the present invention is shown. The mask 10 includes a main mask portion 12 that is shaped to cover substantially the entire face of a patient. The main mask portion 12 includes a conductive element 12a incorporated into the mask as shown, as well as an electrical contact 12b that may be connected to a generator (not shown). As such, the main mask portion 12 functions as an electrode. It should be understood that the electrical contact 12b would be connected to the negative pole of the generator if a negatively charged medicament is applied to the face of the patient in the area covered by the main mask portion 12. On the other hand, the electrical contact 12b would be connected to the positive pole of the generator if a positively charged medicament is applied to the face of the patient in the area covered by the main mask portion 12.

The mask 10 also includes three mask portions 14, 16, 18 that are removeably attached to the main mask portion 12 via perforations or the like. Each of mask portions 14, 16, 18 also include an electrical contact 14a, 16a, 18a (such as a snap connector or the like) so as to function as an electrode. Mask portion 14 is positioned on the lower forehead area of a patient (centered above the eyes) and its electrical contact 14a is connected to the same pole of the generator as electrical contact 12b. Mask portions 16, 18 are positioned bilaterally on the masseter area of a patient and their electrical contacts 16a, 18a are connected to the opposite pole of the generator as electrical contact 12b. The main mask portion 12 must be electrically isolated from each of the mask portions 14, 16, 18. As such, if the main mask portion 12 is coated with a hydrogel or other conductive gel to conform the mask to the skin surface and conduct current from the conductive element in the mask to the underlying tissue, there must be spacing without the conductive gel between the main mask portion 12 and each of the mask portions 14, 16, 18.

It should be understood that the apparatus shown in FIG. 3 may be used to practice the method of the present invention. First, prior to the cosmetic procedure, a negatively or positively charged medicament is applied to substantially the entire face of the patient. The mask 10 (which includes the main mask portion 12 and integrated mask portions 14, 16, 18) is then applied to the face of the patient. Electrical contacts 16a, 18a are connected to one pole of the generator, and electrical contacts 12b and 14a are connected to the opposite pole of the generator (depending on the polarity of the anesthetic medicament). Next, the generator produces a DC current superimposed with either an AC current or a pulsed DC current, which is used to iontophoretically administer the anesthetic medicament and simultaneously provide electroanesthesia to the patient. The length of this "dual anesthesia" period is determined by the rate at which the anesthetic medicament is delivered through the patient's skin and the total dose of medicament that is to be administered.

Prior to commencement of the cosmetic procedure, the main mask portion 12 is removed so as to expose the treatment area for the cosmetic procedure. This may be accomplished by separating the main mask portion 12 from each of the mask portions 14, 16, 18, which are maintained in place during the cosmetic procedure. Finally, during the cosmetic procedure, a DC current superimposed with either an AC current or a pulsed DC current is applied to the electrical contacts 14a, 16a, 18a of mask portions 14, 16, 18 so as to provide electroanesthesia to the patient.

Second Exemplary Embodiment

Figure 4:
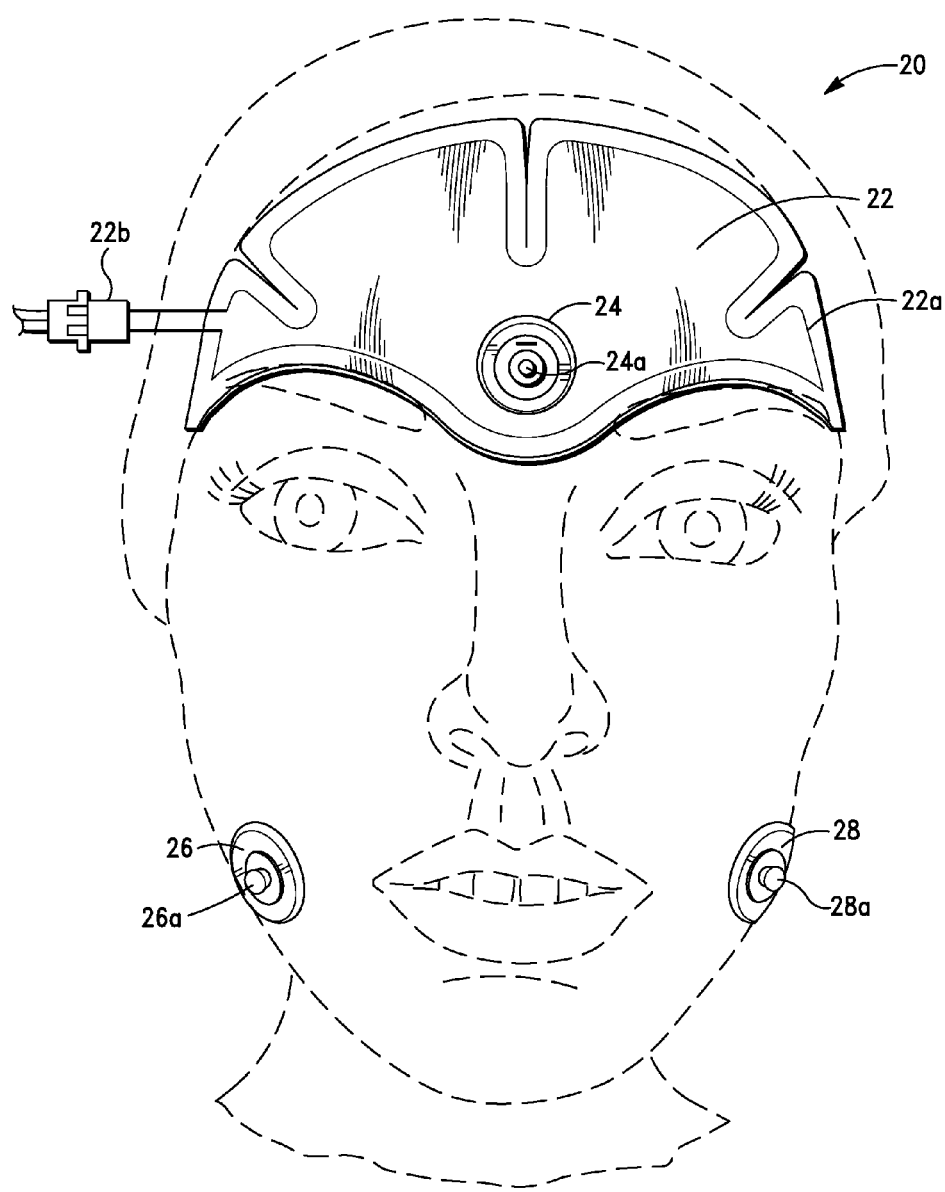
FIG. 4 is a drawing of a conductive mask and associated electrodes in accordance with a second exemplary embodiment of the present invention, wherein the conductive mask includes a main mask portion applied to the forehead area of a patient (which functions as an electrode) and a mask portion positioned on the lower forehead of the patient (which functions as an electrode), and wherein two separate electrodes are positioned bilaterally on the masseter areas of the patient.

Referring to FIG. 4, a conductive mask and associated electrodes in accordance with a second exemplary embodiment of the present invention is shown. The mask 20 includes a main mask portion 22 that is shaped to cover the forehead area of a patient. The main mask portion 22 includes a conductive element 22a incorporated into the mask as shown, as well as an electrical contact 22b that may be connected to a generator (not shown). As such, the main mask portion 22 functions as an electrode. It should be understood that the electrical contact 22b would be connected to the negative pole of the generator if a negatively charged medicament is applied to the forehead area of the patient in the area covered by the main mask portion 22. On the other hand, the electrical contact 22b would be connected to the positive pole of the generator if a positively charged medicament is applied to the forehead area of the patient in the area covered by the main mask portion 22.

The mask 20 also includes a mask portion 24 that is removeably attached to the main mask portion 22 via perforations or the like. The mask portion 24 includes an electrical contact 24a (such as a snap connector or the like) so as to function as an electrode. The mask portion 24 is positioned on the lower forehead area of a patient (centered above the eyes) and its electrical contact 24a is connected to the same pole of the generator as electrical contact 22b. Separate electrodes 26, 28, such as a standard hydrogel or karaya-based electrode, are positioned bilaterally on the masseter area of a patient and their electrical contacts 26a, 28a are connected to the opposite pole of the generator as electrical contact 22b. The main mask portion 22 must be electrically isolated from the mask portion 24. As such, if the main mask portion 22 is coated with a hydrogel or other conductive gel to conform the mask to the skin surface and conduct current from the conductive element in the mask to the underlying tissue, then there must be spacing without the conductive gel between the main mask portion 22 and the mask portion 24.

It should be understood that the apparatus shown in FIG. 4 may also be used to practice the method of the present invention. First, prior to the cosmetic procedure, a negatively or positively charged medicament is applied to the forehead area of the patient. The mask 20 (which includes the main mask portion 22 and integrated mask portion 24) is then applied as shown. Electrical contacts 26a, 28a are connected to one pole of the generator, and electrical contacts 22b and 24a are connected to the opposite pole of the generator (depending on the polarity of the anesthetic medicament). Next, the generator produces a DC current superimposed with either an AC current or a pulsed DC current, which is used to iontophoretically administer the anesthetic medicament and simultaneously provide electroanesthesia to the patient. The length of this "dual anesthesia" period is determined by the rate at which the anesthetic medicament is delivered through the patients skin and the total dose of medicament that is to be administered.

Prior to commencement of the cosmetic procedure, the main mask portion 22 is removed so as to expose the forehead area for the cosmetic procedure. This may be accomplished by separating the main mask portion 22 from the mask portion 24, which is maintained in place during the cosmetic procedure. Finally, during the cosmetic procedure, a DC current superimposed with either an AC current or a pulsed DC current is applied to the electrical contacts 24a, 26a, 28a of mask portion 24 and separate electrodes 26, 28 so as to provide electroanesthesia to the patient.

Third Exemplary Embodiment

Figure 5:
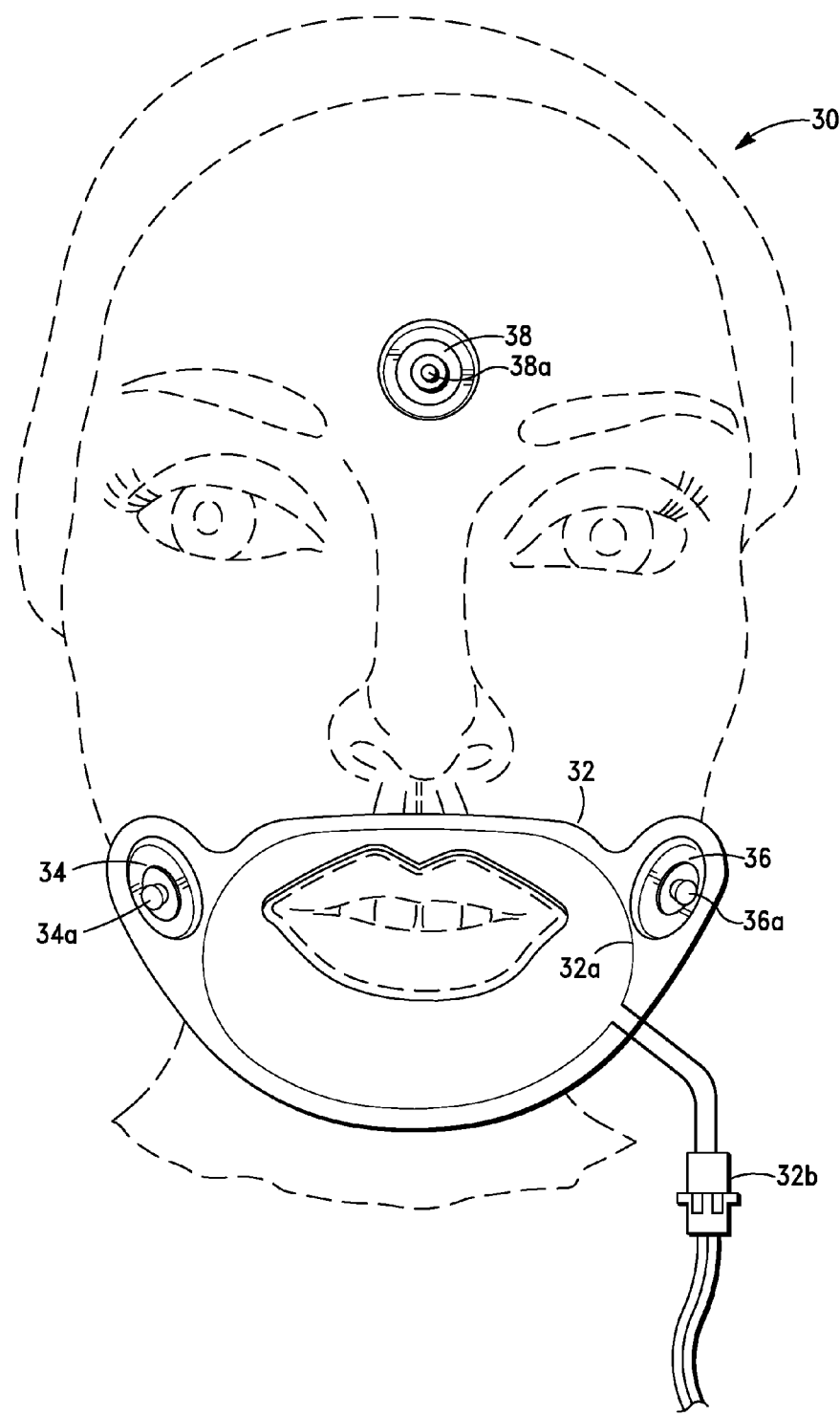
FIG. 5 is a drawing of a conductive mask and an associated electrode in accordance with a third exemplary embodiment of the present invention, wherein the conductive mask includes a main mask portion applied to the lip area of a patient (which functions as an electrode) and two mask portions positioned bilaterally on the masseter areas of the patient (which function as electrodes), and wherein a separate electrode is positioned on the lower forehead of the patient.

Referring to FIG. 5, a conductive mask 30 and associated electrodes in accordance with a third exemplary embodiment of the present invention is shown. The mask 30 includes a main mask portion 32 that is shaped to cover the lip area of a patient. The main mask portion 32 includes a conductive element 32a incorporated into the mask as shown, as well as an electrical contact 32b that may be connected to a generator (not shown). As such, the main mask portion 32 functions as an electrode. It should be understood that the electrical contact 32b would be connected to the negative pole of the generator if a negatively charged medicament is applied to the lip area of the patient in the area covered by the main mask portion 32. On the other hand, the electrical contact 32b would be connected to the positive pole of the generator if a positively charged medicament is applied to the lip area of the patient in the area covered by the main mask portion 32.

The mask 30 also includes two mask portions 34, 36 (not shown), that are removeably attached to the main mask portion 32 via perforations or the like. Each of the mask portions 34, 36 includes an electrical contact 34a, 36a (such as a snap connector or the like) so as to function as an electrode. The mask portions 34, 36 are positioned bilaterally on the masseter area of a patient and their electrical contacts are connected to the opposite pole of the generator as electrical contact 32b. A separate electrode 38, such as a standard hydrogel or karaya-based electrode, is positioned on the lower forehead area of a patient (centered above the eyes) and its electrical contact 38a is connected to the same pole of the generator as electrical contact 32b. The main mask portion 32 must be electrically isolated from the mask portions 34, 36. As such, if the main mask portion 32 is coated with a hydrogel or other conductive gel to conform the mask to the skin surface and conduct current from the conductive element in the mask to the underlying tissue, then there must be spacing without the conductive gel between the main mask portion 32 and the mask portions 34, 36.

It should be understood that the apparatus shown in FIG. 5 may also be used to practice the method of the present invention. First, prior to the cosmetic procedure, a negatively or positively charged medicament is applied to the lip area of the patient. The mask 30 (which includes the main mask portion 32 and integrated mask portions 34, 36) is then applied as shown. Electrical contacts 34a, 36a are connected to one pole of the generator, and electrical contacts 32b, 38a are connected to the opposite pole of the generator (depending on the polarity of the anesthetic medicament). Next, the generator produces a DC current superimposed with either an AC current or a pulsed DC current, which is used to iontophoretically administer the anesthetic medicament and simultaneously provide electroanesthesia to the patient. The length of this "dual anesthesia" period is determined by the rate at which the anesthetic medicament is delivered through the patient's skin and the total dose of medicament that is to be administered.

Prior to commencement of the cosmetic procedure, the main mask portion 32 is removed so as to expose the lip area for the cosmetic procedure. This may be accomplished by separating the main mask portion 32 from the mask portions 34, 36, which are maintained in place during the cosmetic procedure. Finally, during the cosmetic procedure, a DC current superimposed with either an AC current or a pulsed DC current is applied to the electrical contacts 34a, 36a, 38a of the mask portions 34, 36 and separate electrode 38 so as to provide electroanesthesia to the patient.

Fourth Exemplary Embodiment

Figure 6:
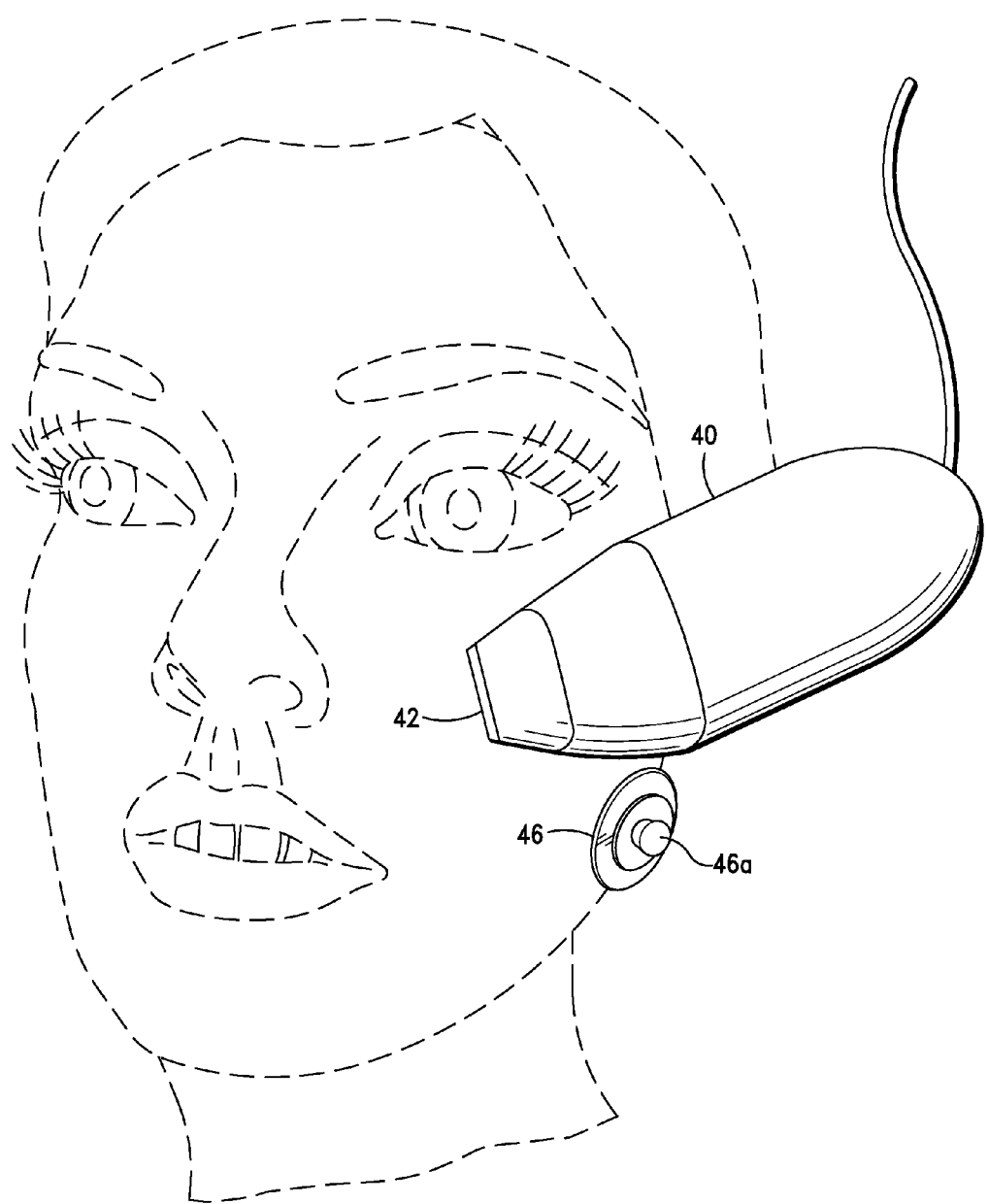
FIG. 6 is a drawing of a Fractal LASER handpiece being applied over a facial area of a patient in accordance with a fourth exemplary embodiment of the present invention, wherein the handpiece includes a conductive applicator (which functions as an electrode) to provide electroanesthesia under the Fractal LASER handpiece during a cosmetic procedure, and wherein two separate electrodes are positioned bilaterally on the masseter areas of the patient.

Referring to FIG. 6, a cosmetic treatment device and associated electrodes in accordance with a fourth exemplary embodiment of the present invention is shown. In this embodiment, the cosmetic treatment device comprises a handpiece 40, such as a Fractal LASER handpiece, that is placed in contact with the skin of a patient during a cosmetic procedure. Coupled to the end or tip of the cosmetic treatment device is a conductive applicator 42. The conductive applicator 42 may comprise, for example, a disposable glass or plastic cap for a Fractal LASER handpiece (as is known in the art), wherein the glass or plastic is doped with a conductor or transparent metal coating. The conductive applicator 42 is press fit or otherwise coupled to a connector in the handpiece 40, which is then electrically connected to a generator (not shown). As such, the conductive applicator 42 functions as an electrode. Separate electrodes 44, 46 (only one of which is shown), such as a standard hydrogel or karaya-based electrode, are positioned bilaterally on the masseter area of a patient and their electrical contacts 44a, 46a are connected to the opposite pole of the generator as conductive applicator 42. The apparatus shown in FIG. 6 may be used to provide electroanesthesia to a patient under the handpiece 40 during a cosmetic procedure (i.e., after the conductive mask has been removed). One skilled in the art will understand that this fourth exemplary embodiment could be implemented in conjunction with any of the first, second or third exemplary embodiments described above, in which case the handpiece 40 and its conductive applicator 42 would replace mask portion 14 (FIG. 3), mask portion 24 (FIG. 4) or separate electrode 38 (FIG. 5).

Fifth Exemplary Embodiment

Figure 7:
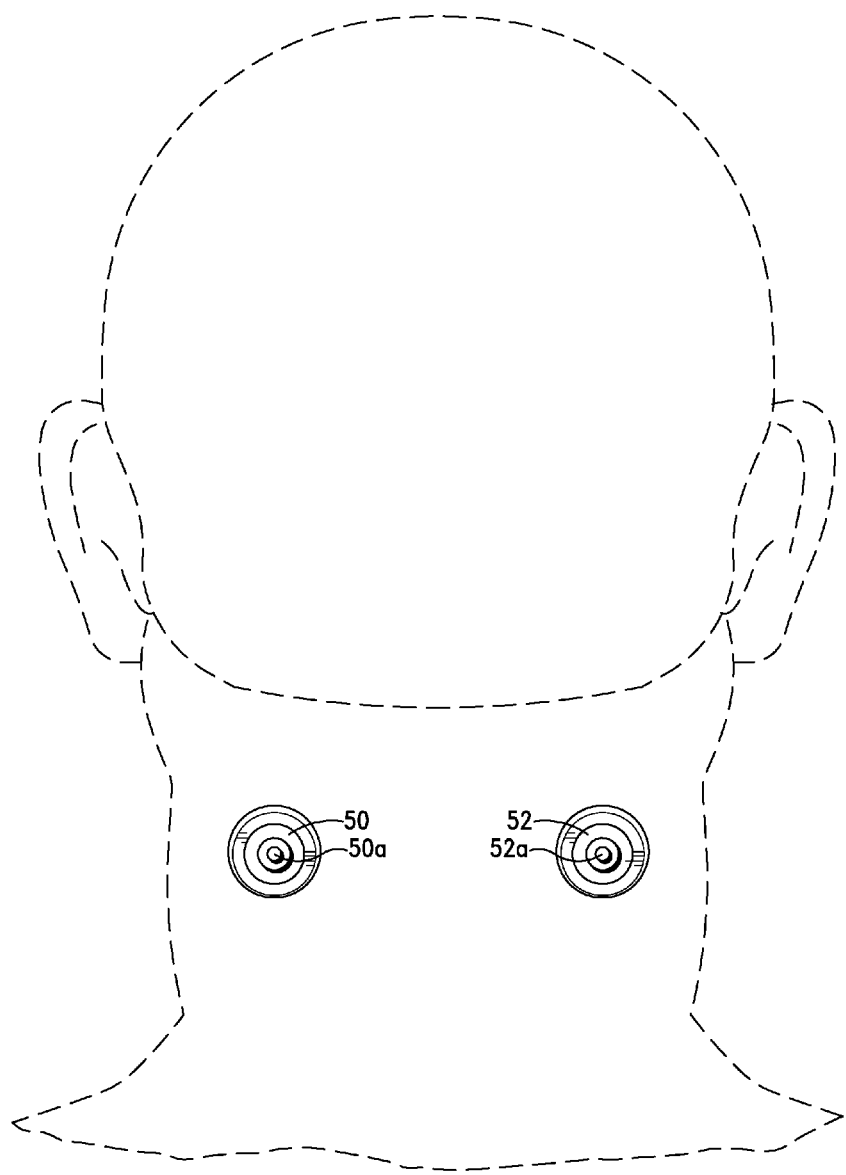
FIG. 7 is a drawing of two separate electrodes positioned bilaterally on the posterior sub-occipital areas of a patient in accordance with a fifth exemplary embodiment of the present invention, wherein this electrode placement may be used as an alternative to the bilateral placement of electrodes on the masseter areas of a patient as shown in FIGS. 3-6.

Referring to FIG. 7, an alternative electrode placement configuration in accordance with a fifth exemplary embodiment of the invention is shown. In this embodiment, two separate electrodes 50, 52, such as a standard hydrogel or karaya-based electrode, are positioned bilaterally on the posterior sub-occipital areas of a patient and their electrical contacts 50a, 52a are connected to a generator (not shown).

The posterior sub-occipital area includes the posterior neck region just lateral to one or more of the cervical vertebrae, most preferably the C1, C2, C3 and/or C4 cervical vertebrae. This electrode placement may be used as an alternative to the bilateral placement of electrodes on the masseter areas of a patient as shown in FIGS. 3-6. In other words, the placement of electrodes 50, 52 on the posterior sub-occipital areas of a patient could be used in place of electrodes 16, 18 (FIG. 3), electrodes 26, 28 (FIG. 4), electrodes 34, 36 (FIG. 5) or electrodes 44, 46 (FIG. 6). Finally, while the embodiments shown in FIGS. 3-7 show the bilateral placement of electrodes on either the masseter or posterior sub-occipital areas of a patient, one skilled in the art will understand that the unilateral placement of such electrodes is also within the scope of the present invention (i.e., you could utilize only one of these pairs of electrodes).

While the invention has been described and illustrated hereinabove with reference to various exemplary embodiments, it should be understood that the invention is not limited to the methodologies or configurations of these embodiments. In addition, although the exemplary embodiments are described as embodying several different inventive features, one skilled in the art will appreciate that any one of these features could be implemented without the others in accordance with the invention. Therefore, the invention is not to be limited to the exemplary embodiments described and illustrated hereinabove, except insofar as such limitations are included in the following claims.

What is claimed and desired to be secured by Letters Patent is as follows:

1. An apparatus for providing electroanesthesia to a patient, comprising:
    a generator operable to produce an electrical current comprised of a direct current superimposed with either an alternating current or a pulsed direct current, wherein the direct current comprises either (a) a negative direct current sufficient to lower a firing threshold of one or more nerves of the patient and wherein the alternating current or pulsed direct current is sufficient to stimulate the one or more nerves of the patient so as to provide the electroanesthesia or (b) a positive direct current sufficient to raise a firing threshold of one or more nerves of the patient and wherein the alternating current or pulsed direct current is sufficient to block the one or more nerves of the patient so as to provide the electroanesthesia; and
    a plurality of electrodes configured to be applied to the skin of the patient, wherein each of the electrodes is connectable to the generator for receiving the electrical current, and wherein one of the electrodes comprises a conductive applicator for a cosmetic treatment device.

2. The apparatus of claim 1 wherein the direct current, alternating current or pulsed DC current is produced at a constant voltage.

3. The apparatus of claim 1 wherein the direct current, alternating current or pulsed DC current is produced at a constant current.

4. The apparatus of claim 1 wherein the direct current, alternating current or pulsed direct current is supplied as a combined voltage limited constant current such that under an increasing impedance the voltage is fixed to a pre-set limit and under a decreasing impedance the voltage decreases to maintain a constant current.

5. The apparatus of claim 1 wherein the carrier frequency of the alternating current ranges from 5 kHz to 200 kHz.

6. The apparatus of claim 5 wherein the carrier frequency is burst modulated in the range of 0.5 Hz to 1000 Hz.

7. The apparatus of claim 1 wherein the direct current is reversed in polarity at fixed intervals to prevent burning of the skin of the patient.

8. The apparatus of claim 7 wherein the direct current or pulsed direct current is ramped down prior to a polarity change and ramped up following the polarity change.

9. The apparatus of claim 1 wherein the direct current optimizes the fluid and pH balance under a treatment area of the patient for optimal coupling of the cosmetic treatment device energy to the treatment area.

10. The apparatus of claim 1 wherein the cosmetic treatment device comprises a laser.

11. The apparatus of claim 1 wherein the cosmetic treatment device comprises a Radio Frequency (RF) or ultrasonic generator.

12. The apparatus of claim 1 wherein the conductive applicator comprises a cap for the cosmetic treatment device.

13. The apparatus of claim 1 wherein the conductive applicator comprises a disposable cap for the cosmetic treatment device.

14. The apparatus of claim 1 wherein a second one of the electrodes comprises:
a conductive mask configured to cover an anesthetic medicament applied to a treatment area on the skin of the patient, wherein the conductive mask includes an electrical contact connectable to the generator for receiving the electrical current.

15. The apparatus of claim 14 wherein the conductive mask is shaped to cover at least a portion of the face of the patient.

16. The apparatus of claim 14 wherein at least a third one of the electrodes is incorporated into a mask portion that is integrated with the conductive mask.

17. The apparatus of claim 16 wherein the conductive mask is separable from the mask portion.

18. The apparatus of claim 14 wherein the electrodes are connected to the generator such that the conductive applicator has the same polarity as the conductive mask and one or a pair of additional electrodes have the opposite polarity as the conductive applicator and the conductive mask.

19. The apparatus of claim 18 wherein the direct current optimizes the fluid and pH balance under the treatment area for optimal coupling of the cosmetic treatment device energy to the treatment area.

20. The apparatus of claim 14 wherein the direct current, alternating current or pulsed direct current is produced at a constant voltage.

21. The apparatus of claim 14 wherein the direct current, alternating current or pulsed direct current is produced at a constant current.

22. The apparatus of claim 14 wherein the direct current, alternating current or pulsed direct current is supplied as a combined voltage limited constant current such that under an increasing impedance the voltage is fixed to a pre-set limit and under a decreasing impedance the voltage decreases to maintain a constant current.

23. The apparatus of claim 14 wherein the carrier frequency of the alternating current ranges from 5 kHz to 200 kHz.

24. The apparatus of claim 23 wherein the carrier frequency is burst modulated in the range of 0.5 Hz to 1000 Hz.

25. The apparatus of claim 14 wherein the direct current or pulsed direct current is reversed in polarity at fixed intervals to prevent burning of the skin of the patient.

26. The apparatus of claim 25 wherein the direct current or pulsed direct current is ramped down prior to a polarity change and ramped up following the polarity change.

27. The apparatus of claim 14 wherein the conductive mask is configured to contact the anesthetic medicament applied to the treatment area on the skin of the patient.

28. The apparatus of claim 27 wherein the electrical current is sufficient to cause the anesthetic medicament to diffuse into tissue underlying the skin of the patient so as to iontophoretically administer the anesthetic medicament.

* * * * *